US009877740B2

(12) United States Patent
Sullivan et al.

(10) Patent No.: US 9,877,740 B2
(45) Date of Patent: Jan. 30, 2018

(54) MORCELLATOR SHIELD WITH DEPLOYABLE BAG

(71) Applicant: MARKET-TIERS INC., Lenexa, KS (US)

(72) Inventors: Theodore J. Sullivan, Lee's Summit, MO (US); Patrick Sullivan, Lenexa, KS (US)

(73) Assignee: MARKET-TIERS INC., Lenexa, KS (US)

( * ) Notice: Subject to any disclaimer, the term of this patent is extended or adjusted under 35 U.S.C. 154(b) by 55 days.

(21) Appl. No.: 14/691,730

(22) Filed: Apr. 21, 2015

(65) Prior Publication Data

US 2015/0297254 A1 Oct. 22, 2015

Related U.S. Application Data

(60) Provisional application No. 61/981,986, filed on Apr. 21, 2014.

(51) Int. Cl.
*A61B 17/32* (2006.01)
*A61B 17/221* (2006.01)
(Continued)

(52) U.S. Cl.
CPC ...... *A61B 17/32002* (2013.01); *A61B 17/221* (2013.01); *A61B 2017/00287* (2013.01);
(Continued)

(58) Field of Classification Search
CPC ........ A61B 17/221; A61B 2090/08021; A61B 2017/2217; A61B 2017/320024;
(Continued)

(56) References Cited

U.S. PATENT DOCUMENTS 4,997,435 A 3/1991 Demeter
5,176,687 A * 1/1993 Hasson ............ A61B 17/00234
606/114
(Continued)

FOREIGN PATENT DOCUMENTS

CN 1718166 1/2006
DE 10 2012 111 821 A1 6/2014
(Continued)

OTHER PUBLICATIONS

U.S. Appl. No. 14/627,722, filed Feb. 20, 2015, Sullivan et al.
(Continued)

*Primary Examiner* — Katrina Stransky
(74) *Attorney, Agent, or Firm* — Stinson Leonard Street LLP

(57) ABSTRACT

A morcellator shield and bag assembly including a shield having a cavity and a bag coupled to the shield. The bag is moveable between a contracted position, in which at least a portion of the bag is positioned within the cavity, and an expanded position. The bag has an opening that is in fluid communication with the cavity when the bag is in the expanded position. A method for using the assembly along with a morcellator to remove tissue from a body cavity. The method includes inserting at least a portion of the assembly into a body cavity, moving the bag to the expanded position, placing tissue in the bag, pulling the bag through an opening in a patient, inserting the morcellator into the assembly, and morcellating the tissue with the morcellator. The assembly is designed to contain the tissue being morcellated and prevent the morcellator from contacting the bag.

27 Claims, 13 Drawing Sheets

(51) Int. Cl.
*A61B 17/00* (2006.01)
*A61B 90/00* (2016.01)

(52) U.S. Cl.
CPC ............... *A61B 2017/2217* (2013.01); *A61B 2017/320024* (2013.01); *A61B 2090/08021* (2016.02)

(58) Field of Classification Search
CPC .... A61B 17/32002; A61B 2017/00287; A61B 2017/00292; A61B 2017/00296; A61B 2017/003; A61B 2017/00305
USPC .......................................... 600/114, 127, 128
See application file for complete search history.

(56) References Cited

U.S. PATENT DOCUMENTS

| | | | |
|---|---|---|---|
| 5,190,561 A | 3/1993 | Graber |
| 5,192,284 A | 3/1993 | Pleatman |
| 5,215,521 A | 6/1993 | Cochran et al. |
| 5,312,416 A | 5/1994 | Spaeth et al. |
| 5,341,815 A | 8/1994 | Cofone et al. |
| 5,368,597 A | 11/1994 | Pagedas |
| 5,370,647 A | 12/1994 | Graber et al. |
| 5,417,697 A | 5/1995 | Wilk et al. |
| 5,443,472 A | 8/1995 | Li |
| 5,464,408 A | 11/1995 | Duc |
| 5,520,634 A | 5/1996 | Fox et al. |
| 5,556,376 A | 9/1996 | Yoon |
| 5,569,284 A | 10/1996 | Young et al. |
| 5,618,296 A | 4/1997 | Sorensen et al. |
| 5,643,282 A | 7/1997 | Kieturakis |
| 5,707,359 A | 1/1998 | Bufalini |
| 5,836,953 A | 11/1998 | Yoon |
| 6,045,566 A | 4/2000 | Pagedas |
| 6,162,235 A | 12/2000 | Vaitekunas |
| 6,270,505 B1 * | 8/2001 | Yoshida ............ A61B 17/00234 606/127 |
| 6,958,069 B2 | 10/2005 | Shipp et al. |
| 8,152,820 B2 | 4/2012 | Mohamed et al. |
| 8,528,563 B2 | 9/2013 | Gruber |
| 2004/0059345 A1 | 3/2004 | Nakao et al. |
| 2004/0158261 A1 * | 8/2004 | Vu .................... A61B 17/00234 606/114 |
| 2010/0217299 A1 | 8/2010 | Williams et al. |
| 2011/0184434 A1 | 7/2011 | Parihar et al. |
| 2011/0184435 A1 | 7/2011 | Parihar et al. |
| 2013/0041359 A1 | 2/2013 | Asselin et al. |
| 2014/0236168 A1 * | 8/2014 | Shibley ............. A61B 17/0218 606/114 |

FOREIGN PATENT DOCUMENTS

| | | |
|---|---|---|
| EP | 1 707 126 A1 | 10/2006 |
| EP | 2 353 511 A1 | 8/2011 |
| EP | 2 436 315 A1 | 4/2012 |
| WO | WO 2011/110836 A2 | 9/2011 |
| WO | WO 2012/026809 A2 | 3/2012 |
| WO | WO 2014/086774 A1 | 6/2014 |

OTHER PUBLICATIONS

Alexander Isakov, Kimberly M. Murdaugh, William C. Burke, Sloan Zimmerman, Ellen Roche, Donal Holland, Jon I. Einarsson and Conor J. Walsh; A New Laparoscopic Morcellator Using an Actuated Wire Mesh and Bag; Jan. 15, 2014; Journal of Medical Devices, vol. 8, Issue 1, Jan. 10, 2009; ASME.

International Search Report and Written Opinion dated Jul. 21, 2015 for PCT/US2015/026771 (10 pages).

* cited by examiner

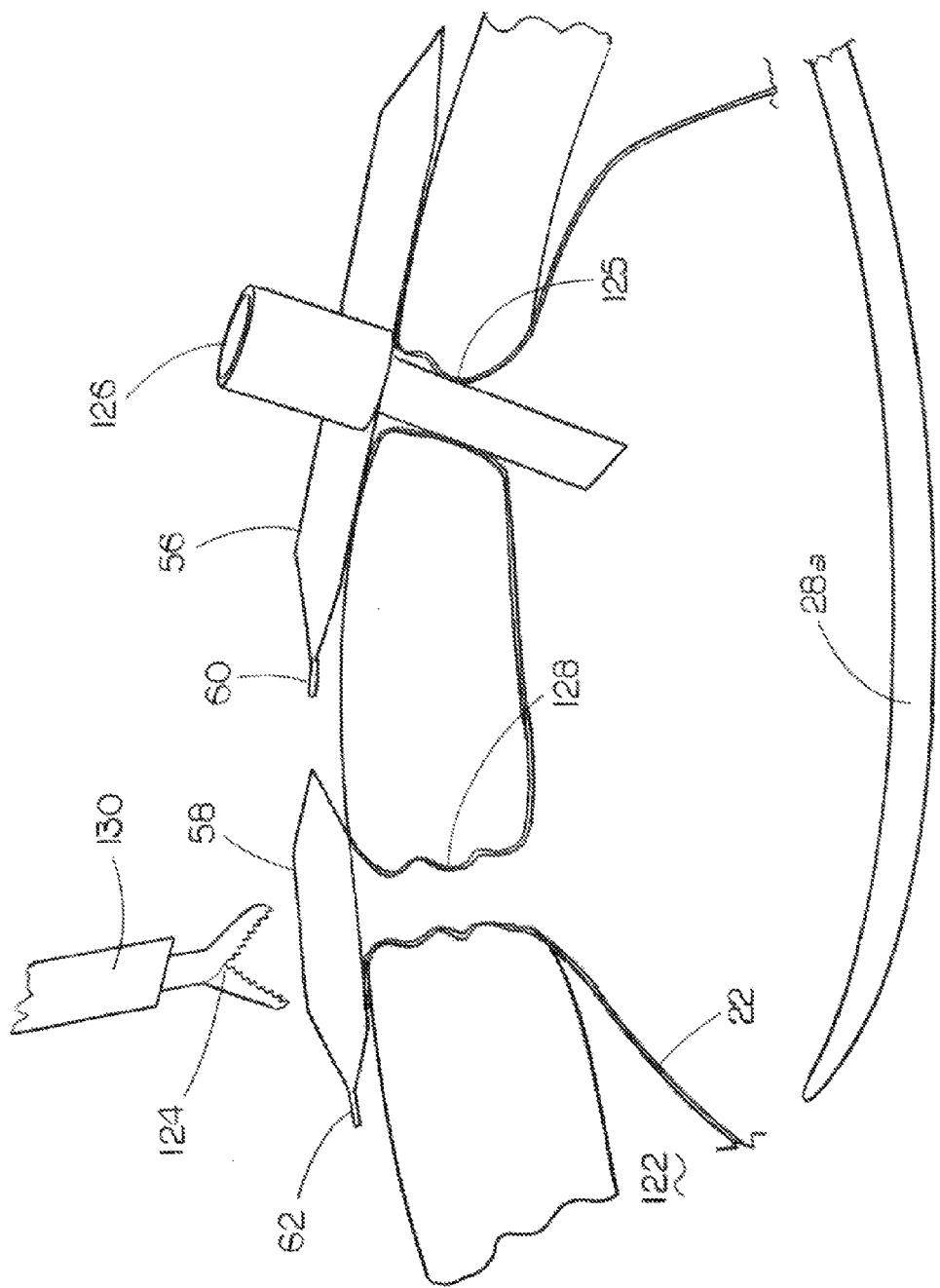

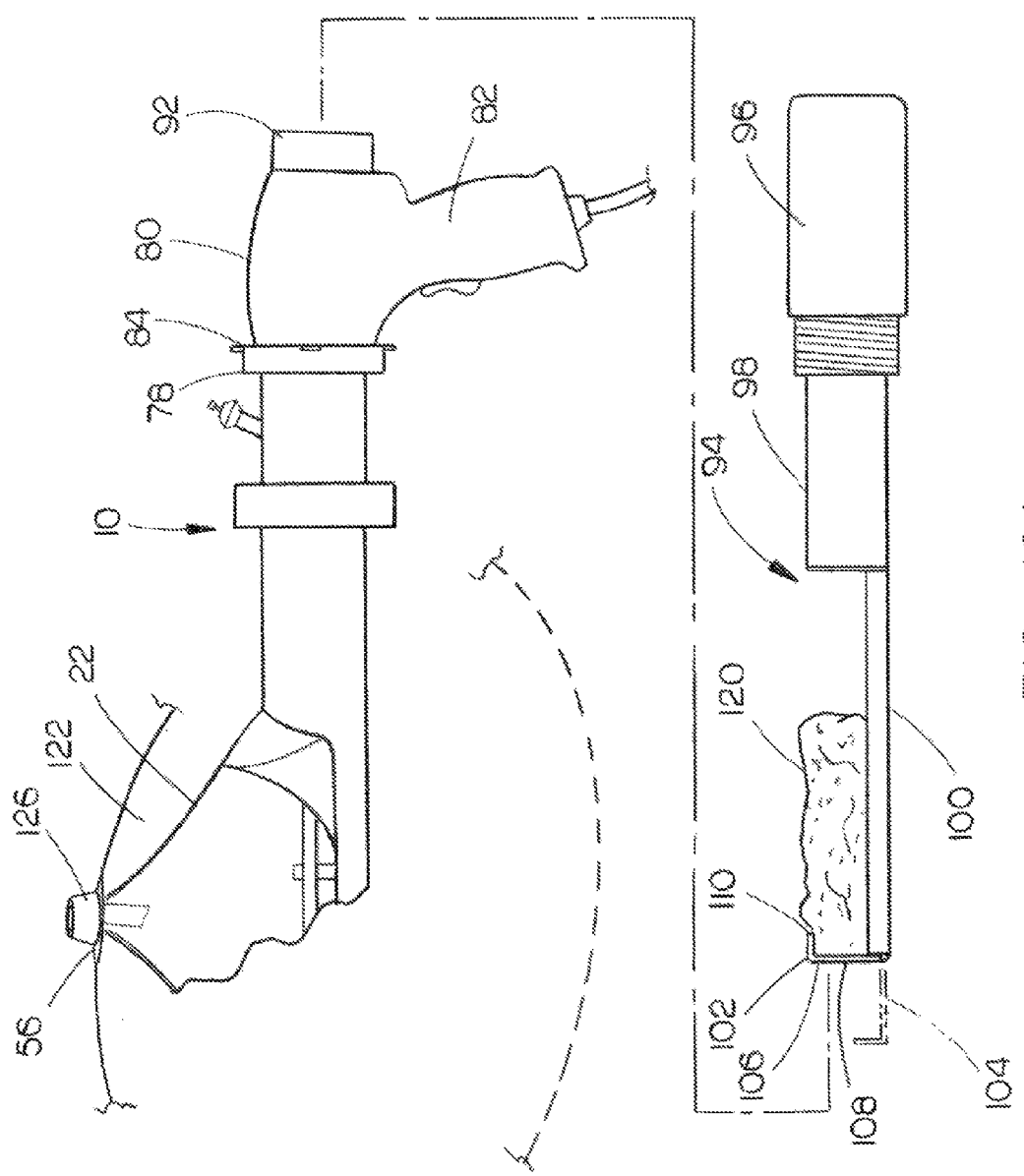

MORCELLATOR SHIELD WITH DEPLOYABLE BAG

CROSS-REFERENCE TO RELATED APPLICATIONS

This application is based on and claims priority to U.S. Provisional Application Ser. No. 61/981,986, filed on Apr. 21, 2014, which is incorporated herein by reference in its entirety.

STATEMENT REGARDING FEDERALLY SPONSORED RESEARCH OR DEVELOPMENT

Not applicable.

BACKGROUND OF THE INVENTION

1. Field of the Invention

The present invention is directed to morcellation, and in particular, to a morcellator shield and bag assembly designed to contain morcellated tissue.

2. Description of Related Art

A morcellator is often used to reduce the size of tissue within a body cavity so that the tissue may be removed from the cavity through a relatively small opening in a minimally invasive proceeding. As disclosed in U.S. Pat. No. 5,836,953 to Yoon and U.S. Patent Application Publication Number 2010/0217299 to Williams, it is known to enclose tissue and a morcellator with a bag for the purpose of containing the tissue as it is morcellated. The devices disclosed in these references, however, would likely not protect the bag from making contact with and being damaged by the morcellator. Further, the devices disclosed in these references are not designed to guide tissue into the morcellator.

BRIEF SUMMARY OF THE INVENTION

The present invention is directed to a morcellator shield and bag assembly including a shield having a cavity, and a bag coupled to the shield. The bag is moveable between a contracted position, in which at least a portion of the bag is positioned within the cavity and an expanded position. The bag has an opening that is in fluid communication with the cavity when the bag is in the expanded position. The morcellator shield and bag assembly is designed for insertion into a body cavity. The assembly is designed to enclose tissue being morcellated inside the body cavity to contain fluid and tissue fragments that may spin away from a morcellator as it morcellates the tissue. In one embodiment, the assembly is designed for insertion vaginally into a peritoneal cavity for removal of a uterus. The shield preferably includes an opening configured to receive a morcellator, and the shield preferably prevents the morcellator from contacting and damaging the bag.

The present invention is also directed to a method of using the morcellator shield and bag assembly along with a morcellator to remove tissue from a body cavity. The method includes inserting at least a portion of the morcellator shield and bag assembly into a body cavity, moving the bag to the expanded position, placing tissue in the bag, pulling at least a portion of the bag through an opening in a patient, inserting at least a portion of the morcellator into the morcellator shield and bag assembly, and morcellating the tissue with the morcellator.

The method preferably includes removing the morcellator from the morcellator shield and bag assembly, closing the opening in the bag, moving the bag to the contracted position, and removing the morcellator shield and bag assembly from the body cavity along with all portions of the tissue. Further, the method may include inserting an instrument into the morcellator shield and bag assembly, guiding the tissue into the morcellator with the instrument, and removing the tissue from the morcellator shield and bag assembly with the instrument.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 9 is a side elevational view showing a trocar sleeve being inserted through an opening in the bag of the assembly of FIG. 1;

FIG. 12A is a side elevational view of the assembly of FIG. 1 showing an instrument withdrawn from the morcellator.

DETAILED DESCRIPTION OF PREFERRED EMBODIMENT

Figure 1:
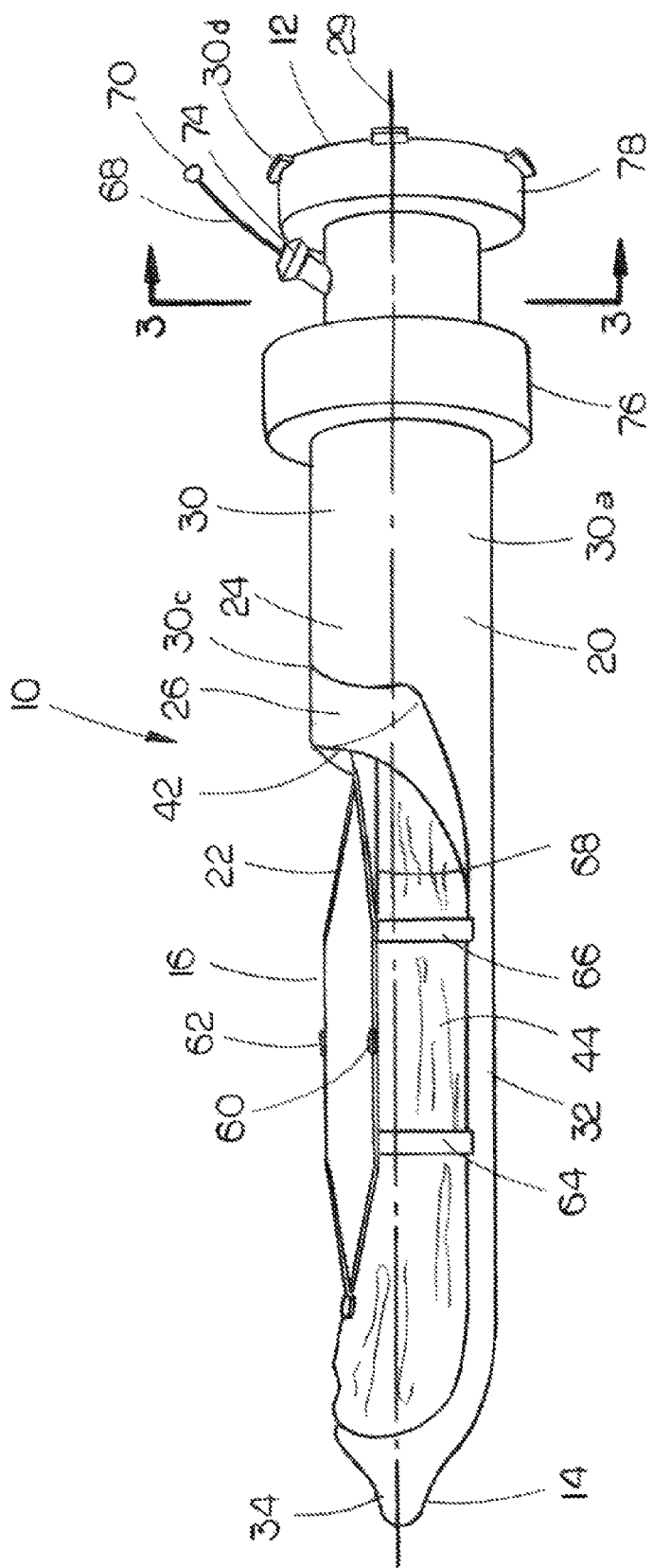
FIG. 1 is a side elevational view of a morcellator shield and bag assembly in accordance with an embodiment of the present invention showing the assembly in a contracted position.

A morcellator shield and bag assembly in accordance with the present invention is identified generally as 10 in FIG. 1. As discussed in more detail below, the assembly 10 is designed for insertion into a body cavity, most preferably for insertion vaginally or cervically into the peritoneal cavity. The assembly 10 is designed to enclose tissue being morcellated inside the body cavity to contain fluid and tissue fragments that may spin away from a morcellator as it morcellates the tissue. Once the subject tissue has been morcellated, the assembly 10 is removed from the body cavity along with any fluid and tissue fragments contained within the assembly 10. Thus, the assembly 10 facilitates complete removal of desired tissue from a body cavity, including any fluid and tissue fragments that may spin away from the morcellator. Complete removal of tissue from a body cavity via assembly 10 is particularly advantageous when it is desired to remove diseased tissue from a body cavity, such as a cancerous uterus, so that no portions of the diseased tissue remain in the body. In addition, assembly 10 is designed to guide tissue into a blade of a morcellator while ensuring that the assembly 10 itself is not damaged by the morcellator. This ensures that no portion of the assembly 10 is punctured by the morcellator blade so that the assembly 10 can effectively contain all of the subject tissue being morcellated and ensure that the tissue is completely removed from the patient.

Referring to FIG. 1, the assembly 10 has a proximal end 12, a distal end 14, a top 16, and a bottom 18. The assembly 10 includes a shield 20 and a bag 22 joined to an outer surface of the shield 20. The shield 20 includes a rigid portion 24, a flexible or semi-flexible hood 26 joined to the rigid portion 24, and flexible wings 28a-b (FIG. 7) joined to the rigid portion 24. A longitudinal axis 29 of assembly 10 extends from the proximal end 12 to the distal end 14 through a center of shield 20.

Figure 3:
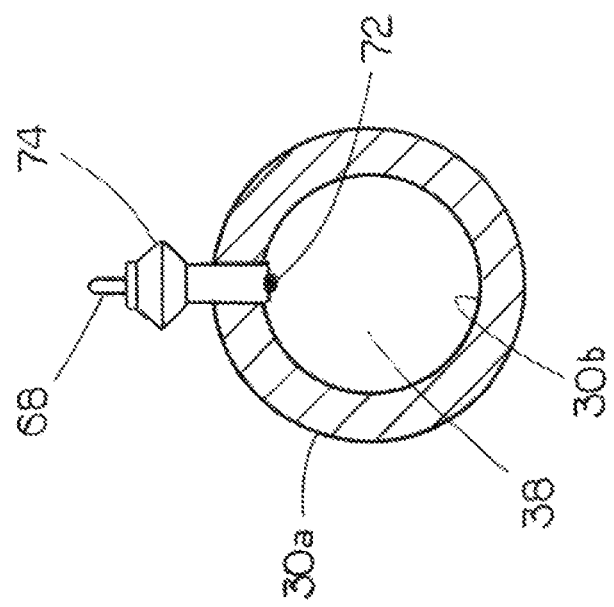
FIG. 3 is a cross-sectional view taken through the line 3-3 of FIG. 1.

Rigid portion 24 includes a hollow cylindrical section 30 extending from proximal end 12 to approximately a midpoint of the assembly 10 along longitudinal axis 29, a lower guide 32 extending from an end 30c of cylindrical section 30 at approximately a midpoint of assembly 10 to distal end 14, and a tip 34 extending from the end of lower guide 32 at distal end 14. Cylindrical section 30 has an outer surface 30a (FIG. 3) and an inner surface 30b. Cylindrical section 30 has first and second ends 30c and 30d (FIG. 1). Cylindrical section 28 has an opening 36, shown in FIG. 4, at proximal end 12. Opening 36 is in fluid communication with a hollow interior 38 (FIG. 3) of cylindrical section 30 through valve 40 (FIG. 4) described in more detail below.

The cross-section of lower guide 32 extends around approximately one-quarter of a circle such that lower guide 32 is approximately one-quarter of a cylinder. Tip 34 extends upward from lower guide 32 so that tip 34 is substantially positioned on the longitudinal axis 29. An opening 42 of shield 20 is defined by lower guide 32 and hood 26. Opening 42 is positioned above lower guide 32 and is in fluid communication with a cavity 44 of shield that is partially surrounded by lower guide 32. Hollow interior 38 (FIG. 3) of cylindrical section 30 forms a portion of cavity 44. Assembly 10 is preferably inserted into a patient such that tip 34 enters the patient first and proximal end 12 is positioned outside the patient. Inside the patient, assembly 10 is preferably oriented such that bag 22 is above lower guide 32. It is within the scope of the invention for tip 34 to be omitted from assembly 10.

Hood 26 is joined to an edge of the end 30c of cylindrical section 30 and to an upper edge of lower guide 32. Hood 26 is made from a flexible or semi-flexible material such that it is moveable between the contracted position shown in FIG. 1 and the expanded position shown in FIG. 2 when bag 22 is deployed as described in more detail below. When in the contracted position, hood 26 is shaped as approximately three-quarters of a cylinder and forms a complete cylinder with the portion of lower guide 32 to which it is joined. Hood 26 has a forward edge 46 (FIG. 2) that tapers from its connection to lower guide 32 upward so that the portion of forward edge 46 joined to lower guide 32 is positioned farther from the end 30c of cylindrical section 30 than the portion of forward edge 46 at the top 16 of assembly 10. Hood 26 is positioned to protect bag 22 from potential damage by a morcellator, as described in more detail below.

Figure 7:
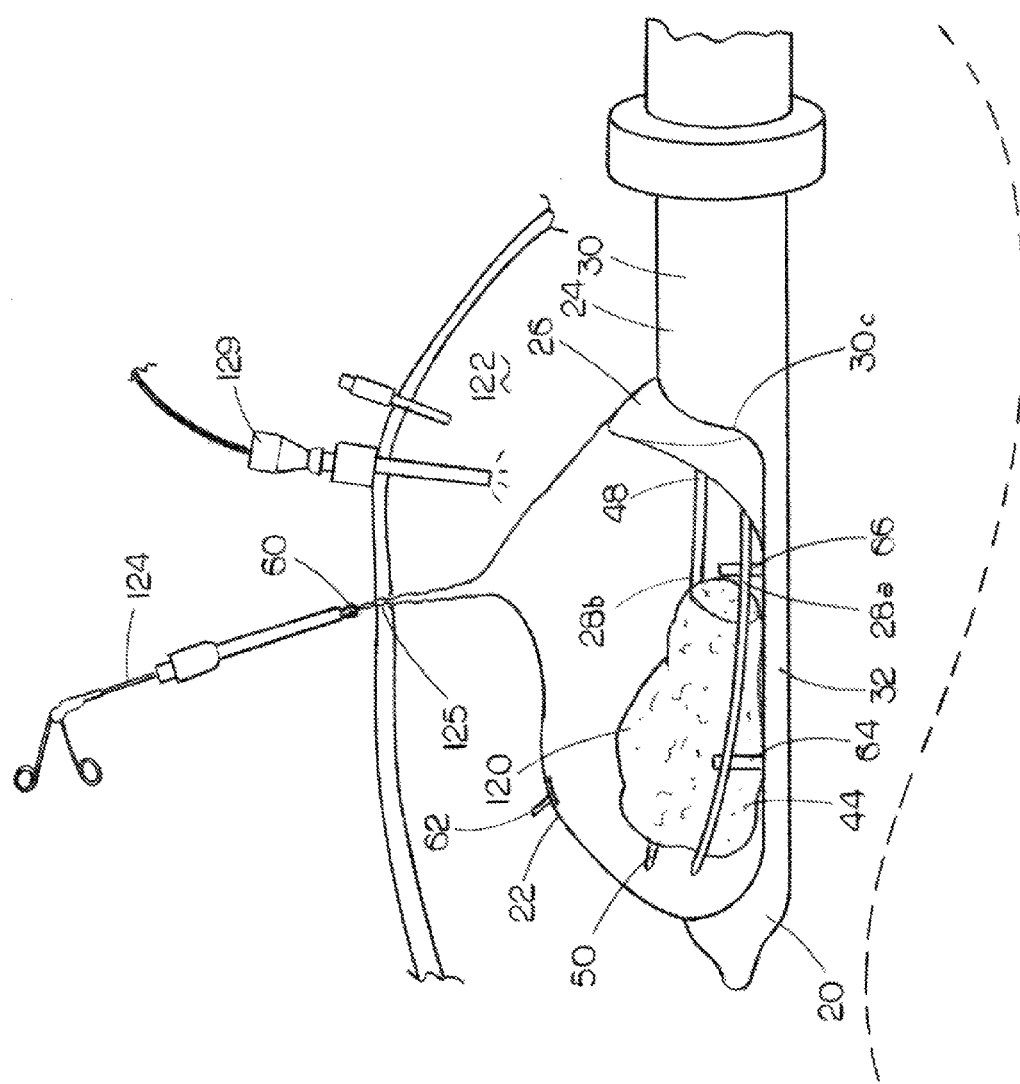
FIG. 7 is a side elevational view of the assembly of FIG. 1 showing the assembly inserted partially into a patient's vaginal canal and a portion of the bag being pulled through an opening in the patient's abdomen.

Wings 28a-b, shown in FIG. 7, are preferably elongate strips of material. Wings 28a-b may have any cross-sectional shape, including rectangular or circular. Wings 28a-b are moveable between a contracted position in which they are positioned within cavity 44 (FIG. 1) of shield 20 and an expanded position, shown in FIG. 7, in which they at least partially extend outward from cavity 44. Each of the wings 28a-b has a proximal end, one of which is shown as 48, that is joined to end 30c of cylindrical section 30 at approximately a midpoint of assembly 10 and a distal, free end, one of which is shown as 50. Wings 28a-b are preferably joined to cylindrical section 30 by bonding or adhesive; however, it is within the scope of the invention for the wings 28a-b to be joined to cylindrical section 30 in any manner. Wings 28a-b are preferably parallel to longitudinal axis 29 when in the contracted position.

Wings 28a-b are joined to cylindrical section 30 in a manner that permits wings 28a-b to bend at an angle with respect to cylindrical section 30 when the wings 28a-b are in the expanded position shown in FIG. 7 such that the wings 28a-b are non-parallel to longitudinal axis 29. The material from which the wings 28a-b are made also preferably permits the wings 28a-b to bend at an angle with respect to cylindrical section 30 and permits the wings 28a-b themselves to flex along their length so that they are curved or non-planar. Wings 28a-b may preferably bend and/or flex in any direction with respect to cylindrical section 30 and flex into curved shapes in order to accommodate the placement of tissue within bag 22 and cavity 44 when bag 22 and wings 28a-b are in the expanded position. The wings 28a-b when in their expanded position assist in spacing the sides of bag 22 apart and away from shield 20 in order to create sufficient space within the bag 22 to morcellate tissue within the bag 22 without making contact between the morcellator and bag 22.

Wings 28a-b may be joined to cylindrical section 30 and/or formed in such a manner that they are naturally biased toward the expanded position shown in FIG. 7. In this case, a wing releasing structure, described below, may hold the wings 28a-b in the contracted position until it is desired to expand the wings 28a-b to the expanded position. The wing releasing structure, described below, may be moveable between a position in which it holds the wings 28a-b in the contracted position and a position in which it releases the wings 28a-b to the expanded position. As discussed below, bag 22, arms 64 and 66, cord 68, and clamp 74 may form a portion of the wing releasing structure.

Bag 22 is a thin flexible membrane that is attached to an outer surface of lower guide 32 surrounding opening 42 and to an outer surface of flexible hood 26. A first end 52 (FIG. 2) of bag 22 is attached to outer surfaces of lower guide 32 and flexible hood 26 so that no portion of bag 22 is positioned within cavity 44 when the bag 22 is deployed to the expanded position shown in FIG. 2. This ensures that the bag 22 is not damaged by a morcellator when in the expanded position. Bag 22 may also be joined to outer surfaces of wings 28a-b and an outer surface of cylindrical section 30. First end 52 of bag 22 is joined to shield 20 in a manner that forms a seal between bag 22 and shield 20 to prevent ingress or egress of fluid and tissue between bag 22 and shield 20. Bag 22 is moveable to the expanded position shown in FIG. 2 from the contracted position shown in FIG. 1, in which the majority of bag 22 is positioned within the cavity 44 of shield 20. Bag 22 is preferably in the contracted position when the assembly 10 is inserted into and removed from a patient. Bag 22 is moveable to the contracted position so that the assembly 10 has a relatively small cross-sectional area when inserted into and removed from a patient and to protect bag 22 from damage when the assembly 10 is inserted into and removed from a patient.

Figure 2:
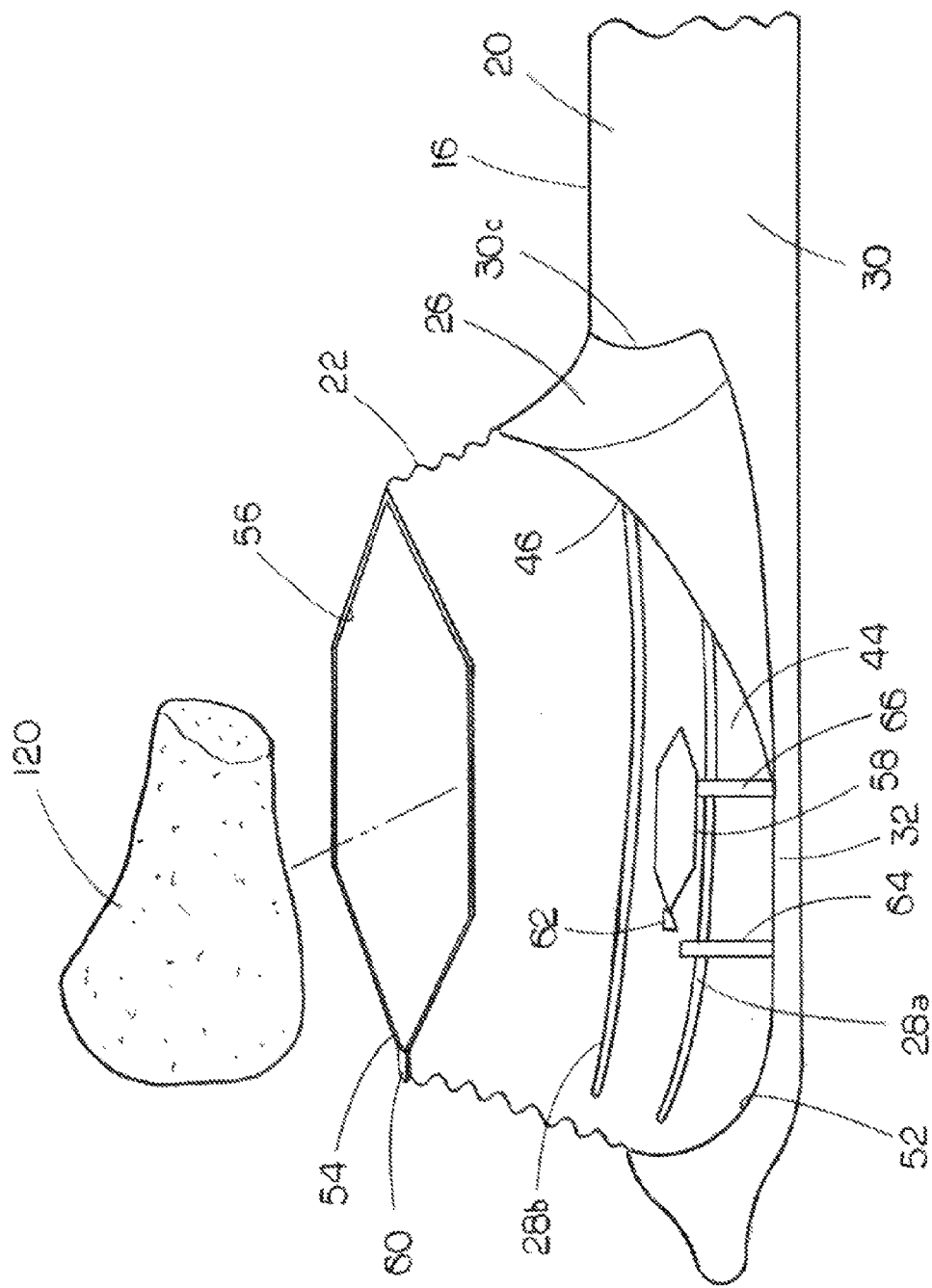
FIG. 2 is a partial side elevational view of the assembly of FIG. 1 showing the assembly in an expanded position and a uterus being placed within a bag of the assembly.

Bag 22 has a second end 54 spaced from proximal end 52 when bag 22 is in the expanded position. Bag 22 has a first opening 56 at its second end 54 to permit tissue to enter an interior of bag 22 and cavity 44. Bag 22 also has a second opening 58 (shown in the background in FIG. 2) also positioned at the second end 54 of bag 22. While FIG. 2 shows opening 56 with a trapezoidal shape, the opening 56, as well as opening 58, may be manipulated to any desired shape. A first tab 60 is joined to bag 22 adjacent first opening 56, and a second tab 62 is joined to bag 22 adjacent second opening 58. Tabs 60 and 62 are attached to bag 22 in such a manner that they may be grasped to pull bag 22 through an opening in a patient's abdominal cavity, as described in more detail below and shown in FIG. 7, which moves bag 22 from the contracted position shown in FIG. 1 to the expanded position shown in FIG. 2. The second end 54 of bag 22 and the first and second openings 56 and 58 are positioned outside of cavity 44 when the bag 22 is in the expanded position.

Bag 22 preferably includes first and second closing structures adjacent to the first and second openings 56 and 58, respectively. Each of the closing structures may include interlocking channels (not shown) formed in the bag 22 surrounding the respective opening 56 and 58 that mate to seal the opening 56 and 58. Each of the closing structures may include a slide lock (not shown) that is moved across the respective opening 56 and 58 to mate the channels and seal the opening 56 and 58 in a similar manner as is known with respect to conventional plastic bags used for food storage and other purposes. The closing structures are thus capable of moving the respective openings 56 and 58 from an open position to a closed position. Each of tabs 60 and 62 may be a slide lock that is used to close and seal openings 56 and 58, respectively.

When the expanded position, the interior of bag 22 is in fluid communication with cavity 44, the hollow interior 38 (FIG. 3) of cylindrical section 30 and opening 36 (FIG. 4) through valve 40. When in the open position, each of openings 56 and 58 is in fluid communication with the interior of bag 22 and cavity 44. When each of the openings 56 and 58 is in its closed position, the interior of bag 22 and cavity 44 are sealed such that they are only accessible through valve 40 and so that material cannot leak out of the bag 22. Bag 22 is preferably attached to hood 26, wings 28a-b, lower guide 32, and cylindrical section 30 with adhesive and/or by bonding in another manner; however, bag 22 may be attached to hood 26, wings 28a-b, lower guide 32, and cylindrical section 30 in any suitable manner.

Figure 6:
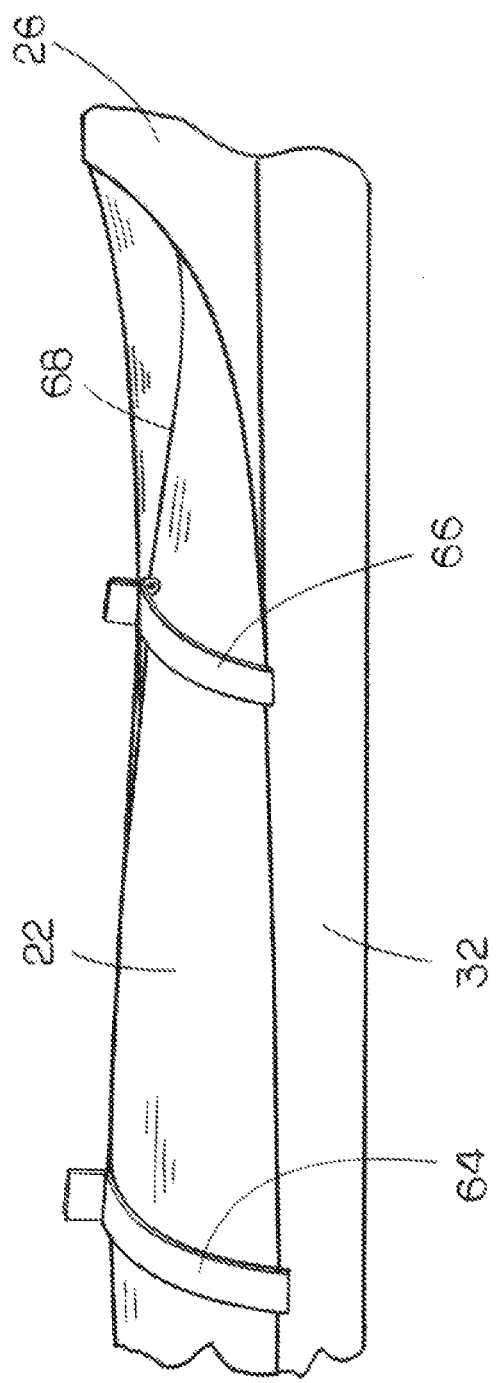
FIG. 6 is a side elevational view showing a bag release system of the assembly of FIG. 1.

As shown in FIG. 1, arms 64 and 66 are attached to lower guide 32. Arms 64 and 66 are preferably rigidly attached to lower guide 32 and loosely attached to a portion of bag 22, as shown in FIG. 6, when bag is in the contracted position. The arms 64 and 66 extend from the lower guide 32 around and over a portion of the bag 22 sufficient to retain the bag 22 in its contracted position within cavity 44 when the assembly 10 is inserted into a patient. The loose connection between the arms 64 and 66 and bag 22 may be broken when the assembly 10 is positioned within a patient for the purpose of deploying bag 22 from the contracted position to the expanded position shown in FIG. 2. This loose connection between arms 64 and 66 and bag 22 may be broken by grasping the arms 64 and 66 with an instrument and pulling them away from bag 22 or by grasping and pulling one of tabs 60 and 62.

The loose connection between the arms 64 and 66 and bag 22 may alternatively be broken by pulling a cord 68 that is loosely attached to arms 64 and 66 at the locations where the arms 64 and 66 are connected to bag 22. Cord 68 extends from a proximal end 70 through an opening 72 (FIG. 3) in cylindrical section 30. From opening 72, cord 68 extends along inner surface 30b of cylindrical section 30 adjacent the top 16 of assembly 10 to arms 64 and 66. Cylindrical section 30 may include structure (not shown) such as a channel, hooks, or rings, that encloses and/or guides cord 68 through assembly 10.

Cord 68 passes through a clamp 74, shown in FIG. 1, which is attached to cylindrical section 30 near proximal end 12. The clamp 74 is movable between a clamped position that prevents movement of the cord 68 through clamp 74 and an unclamped position that allows cord 68 to move through clamp 74. Clamp 74 may be moved to the unclamped position so that cord 68 can be pulled through clamp 74 in order to break the loose connection between bag 22 and arms 64 and 66, which allows bag 22 to deploy to its expanded position. Arms 64 and 66, cord 68, and bag 22 may form a part or all of the wing releasing structure referred to above. For example, when arms 64 and 66 are loosely joined to bag 22, arms 64 and 66 and bag 22 may hold wings 28a-b in their contracted position. When the cord 68 is pulled to break the connection between arms 64 and 66 and bag 22, the wings 28a-b may be allowed to move to their expanded position as the bag 22 is pulled out of cavity 44 and moved to its expanded position. The wings 28a-b may themselves expand the bag 22 to its expanded position when arms 64 and 66 are disconnected from bag 22, or alternatively, the wings 28a-b may merely assist in expansion of bag 22 as one of tabs 60 and 62 is grasped and bag 22 is pulled from cavity 44. Wings 28a-b are in the contracted position when the bag 22 is in the contracted position, and wings 28a-b are in the expanded position when the bag 22 is in the expanded position.

It is within the scope of the invention for wings 28a-b to be omitted from assembly 10. Arms 64 and 66, cord 68, and clamp 74 may also be omitted from assembly. In such a construction, bag 22 may simply be folded and pressed within cavity 44 in a manner that retains bag 22 within cavity 44 until bag 22 is grasped and pulled from cavity 44.

As shown in FIG. 1, assembly 10 also includes a sponge 76 or balloon, which is ring-shaped and positioned around cylindrical section 30 near proximal end 12. Sponge 76 preferably assists in sealing the opening in the patient's body through which assembly 10 is inserted to prevent loss of pressure within the body cavity in which assembly 10 is in use. For example, sponge 76 may assist in sealing the vaginal opening to prevent loss of pneumoperitoneum during a surgical procedure.

Figure 4:
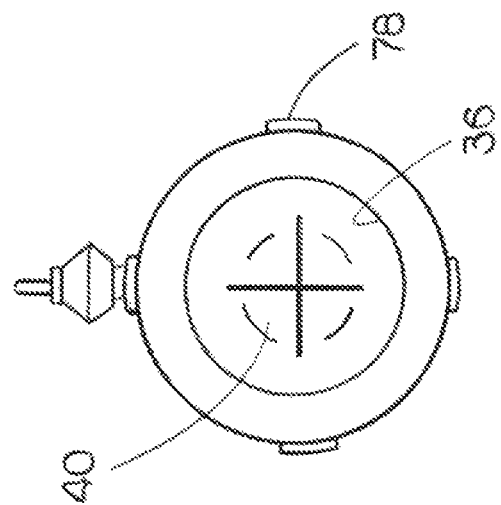
FIG. 4 is a rear elevational view of the assembly of FIG. 1.

A morcellator connector 78, shown in FIGS. 1 and 4, is joined to cylindrical section 30 at the proximal end 12 of assembly 10. Morcellator connector 78 may have any suitable structure necessary to releasably connect assembly 10 to a morcellator 80, as shown in FIG. 12A.

Valve 40, shown in FIG. 4, is positioned inside of the proximal end 12 of cylindrical section 30 for preventing loss of pressure within the body cavity in which assembly 10 is in use. Valve 40 forms a seal within the hollow interior 38 of cylindrical section 30 that prevents the free flow of fluid from cavity 44 through opening 36. Valve 40 preferably includes flaps with slits positioned between the flaps that allow an instrument to be inserted through the flaps. When an instrument is inserted through valve 40, such as a portion of morcellator 80, the flaps preferably move to allow insertion of the instrument and seal against the outer surface of the instrument to form a seal between the instrument and valve 40. Valve 40 is preferably made from a resilient material that moves back to a closed position that seals the inside of cylindrical section 30 when an instrument is no longer inserted through it. Valve 40 and morcellator connector 78 are optional depending on what type of morcellator 80 or other instrument is used in conjunction with assembly 10.

Bag 22 is preferably made from medical grade flexible ballistic plastic. Rigid portion 24 is preferably made from medical grade rigid ballistic plastic. Hood 26 is preferably made from medical grade flexible or semi-flexible ballistic plastic. Wings 28a-b are preferably made from medical grade flexible ballistic plastic. It is within the scope of the invention for bag 22, rigid portion 24, hood 26, and flexible wings 28a-b to be made from any other suitable materials. Bag 22, rigid portion 24, hood 26, and flexible wings 28a-b are preferably formed from a clear material so that a surgeon may view what is inside assembly 10 during a surgical procedure. The diameter of shield 20 is preferably between approximately 15 to 35 mm, and is most preferably approximately 30-35 mm; however, it is within the scope of the invention for shield 20 to have any diameter. This diameter of shield 20 refers to the cross-sectional diameter of outer surface 30a (FIG. 3) of cylindrical section 30.

Figure 5:
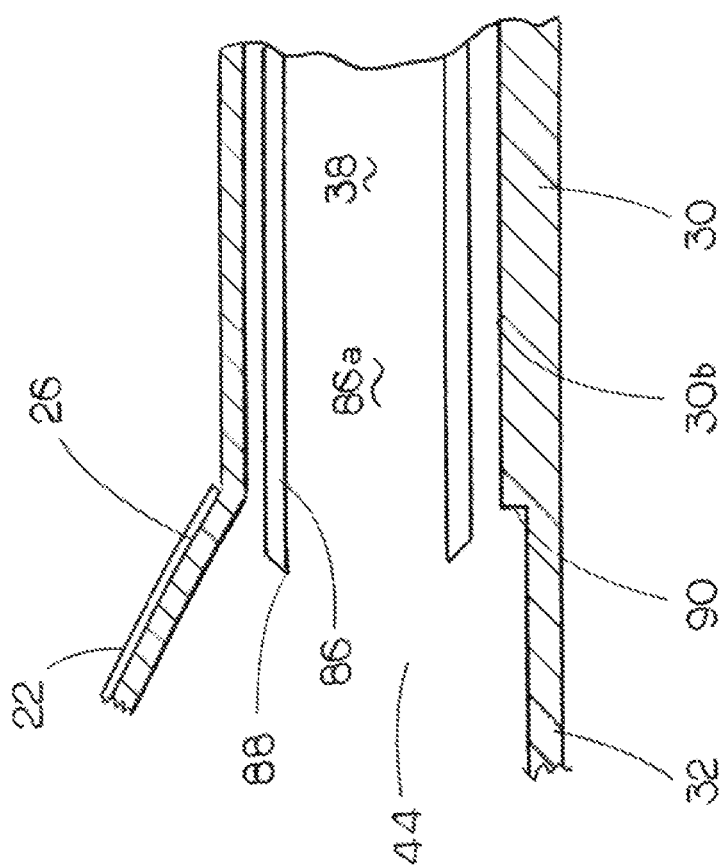
FIG. 5 is a schematic view showing a morcellator blade within the assembly of FIG. 1.

Assembly 10 is preferably configured for use with morcellator 80, as shown in FIG. 12A. Morcellator 80 is preferably a morcellator manufactured for Blue Endo, LLC by Trokamed; however, morcellator 80 may be any type of morcellator. Further, it is within the scope of the invention for assembly 10 to be used on its own or with another type of surgical device besides a morcellator 80 such as a mono or bipolar cutting mechanism or loop. Morcellator 80 includes a housing 82 that may be grasped by an operator. Housing 82 includes a connector 84 at one end that is operable to releasably engage morcellator connector 78 of assembly 10. Morcellator 80 includes a blade 86 (FIG. 5) that extends through the opening 36, hollow interior 38, and valve 40 in assembly 10. Blade 86 has a cutting edge 88 shown in FIG. 5 that is positioned at approximately the region where lower guide 32 extends outward from cylindrical section 30. At the transition from cylindrical section 30 to lower guide 32 within assembly 10, there is a step 90 where the inner diameter of lower guide 32 is greater than the inner diameter of inner surface 30b of cylindrical section 30 to provide increased clearance between cutting edge 88 and lower guide 32 and facilitate morcellation of tissue within cavity 44.

Blade 86 is preferably moveable within cavity 44 solely in a direction aligned with the longitudinal axis 29 of assembly 10; however, blade 86 cannot move through cavity 44 beyond lower guide 32 to a position where it would come into contact with bag 22. Morcellator 80 releasably engages assembly 10 in such a manner that blade 86 is preferably not moveable with respect to assembly 10 in a direction perpendicular to the longitudinal axis 29 of assembly 10 so that cutting edge 88 remains within cavity 44 and does not come into contact with hood 26, wings 28a-b, lower guide 32, and/or bag 22 during use. During use blade 86 remains within cavity 44 in a position where blade 86 will not contact bag 22 when bag 22 is in the expanded position as hood 26, lower guide 32, and wings 28a-b space bag 22 away from blade 86 and prevent blade 86 from contacting bag 22.

Morcellator blade 86 is tubular with a hollow interior 86a (FIG. 5) that is in fluid communication with cavity 44. Housing 82 of morcellator 80 includes a hollow channel (not shown) that is in fluid communication with the hollow interior 86a of blade 86 and cavity 44. The hollow channel of housing 82 terminates at a valve 92 (FIG. 12A), which may be similar to valve 40 described above. Morcellator 80 is operable to rotate morcellator blade 86 within cavity 44 in order to cut tissue within cavity 44 into fine particles that may be removed from cavity 44 through the hollow interior 86a of blade 86 and valve 92.

Referring to FIG. 12A, an instrument 94 may be inserted through the valve 92 and hollow interior 86a of blade 86 into cavity 44 for pulling tissue toward blade 86, through the hollow interior 86a of blade 86, and out of morcellator 80 and assembly 10 through valve 92. Instrument 94 includes a handle 96 at a proximal end that may be grasped by an operator to move the instrument 94 in a direction that is aligned with the longitudinal axis 29 of assembly 10. A stabilizer 98 is joined to handle 96 adjacent proximal end. Stabilizer 98 is a cylinder with an outer diameter that is approximately equal to an inner diameter of the hollow channel within the housing 82 of morcellator 80 such that when stabilizer 98 is inserted through valve 92 into the hollow channel within housing 82, instrument 94 may not be moved with respect to morcellator 80 in a direction that is perpendicular to the longitudinal axis 29 of assembly 10. Thus, stabilizer 98 ensures that instrument 94 may only be moved in a direction that is parallel to longitudinal axis 29.

Instrument 94 includes an elongate shaft 100 extending outward from stabilizer 98 and an L-shaped grasper 102 connected to the end of shaft 100 at a distal end of instrument 94. L-shaped grasper 102 is moveable between a first position shown as 104 in FIG. 12A, in which it is substantially aligned with shaft 100, and a second position shown as 106 in FIG. 12A, in which it extends upward in a direction that is perpendicular to shaft 100. Grasper 102 is preferably connected to a lever (not shown) provided on handle 96 that is operable to move the grasper 102 between the first and second positions. L-shaped grasper 102 may be inserted through valve 92 into cavity 44 within bag 22 with the grasper 102 in the first position 104. The stabilizer 98 ensures that the grasper 102 and shaft 100 remain adjacent lower guide 32 as grasper 102 and shaft 100 enter cavity 44 to prevent grasper 102 from contacting and puncturing bag 22. The stabilizer 98 prevents movement of the grasper 102 and shaft 100 in a direction that is perpendicular to the longitudinal axis 29 of assembly 10 so that the grasper 102 cannot come into contact with and puncture bag 22. As the stabilizer 98 is inserted into morcellator 80, a stop (not shown) within morcellator 80 engages stabilizer 98 to prevent further insertion of instrument 94. The lengths of shaft 100 and grasper 102 are such that when stabilizer 98 engages the stop (not shown) within morcellator 80, grasper 102 when in the first position 104 does not extend beyond the distal end of lower guide 32 so that grasper 102 does not contact and puncture bag 22.

Figure 10:
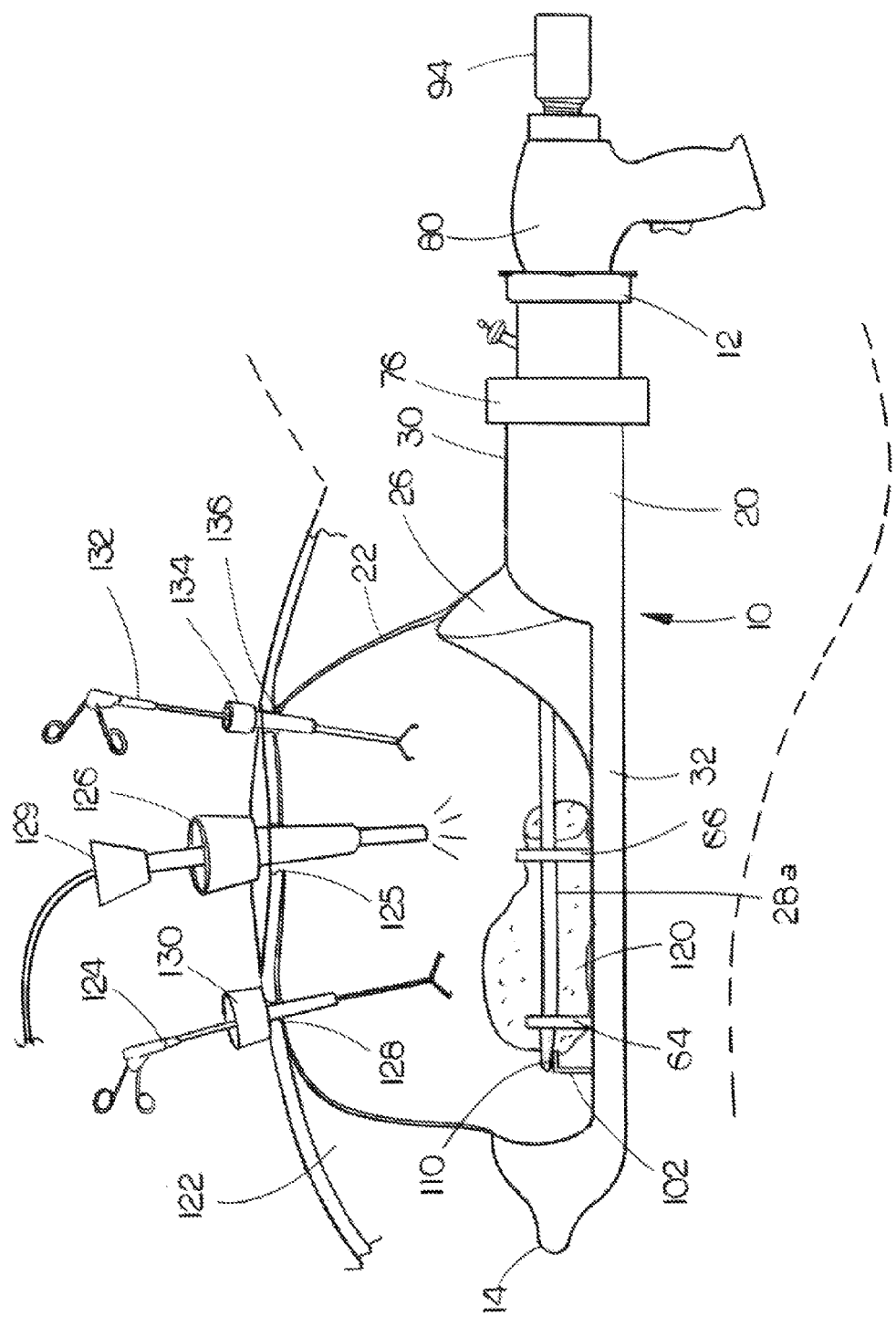
FIG. 10 is a side elevational view of the assembly of FIG. 1 showing a plurality of trocar sleeves inserted through openings in a patient's abdomen and through openings in the bag.
Figure 11:
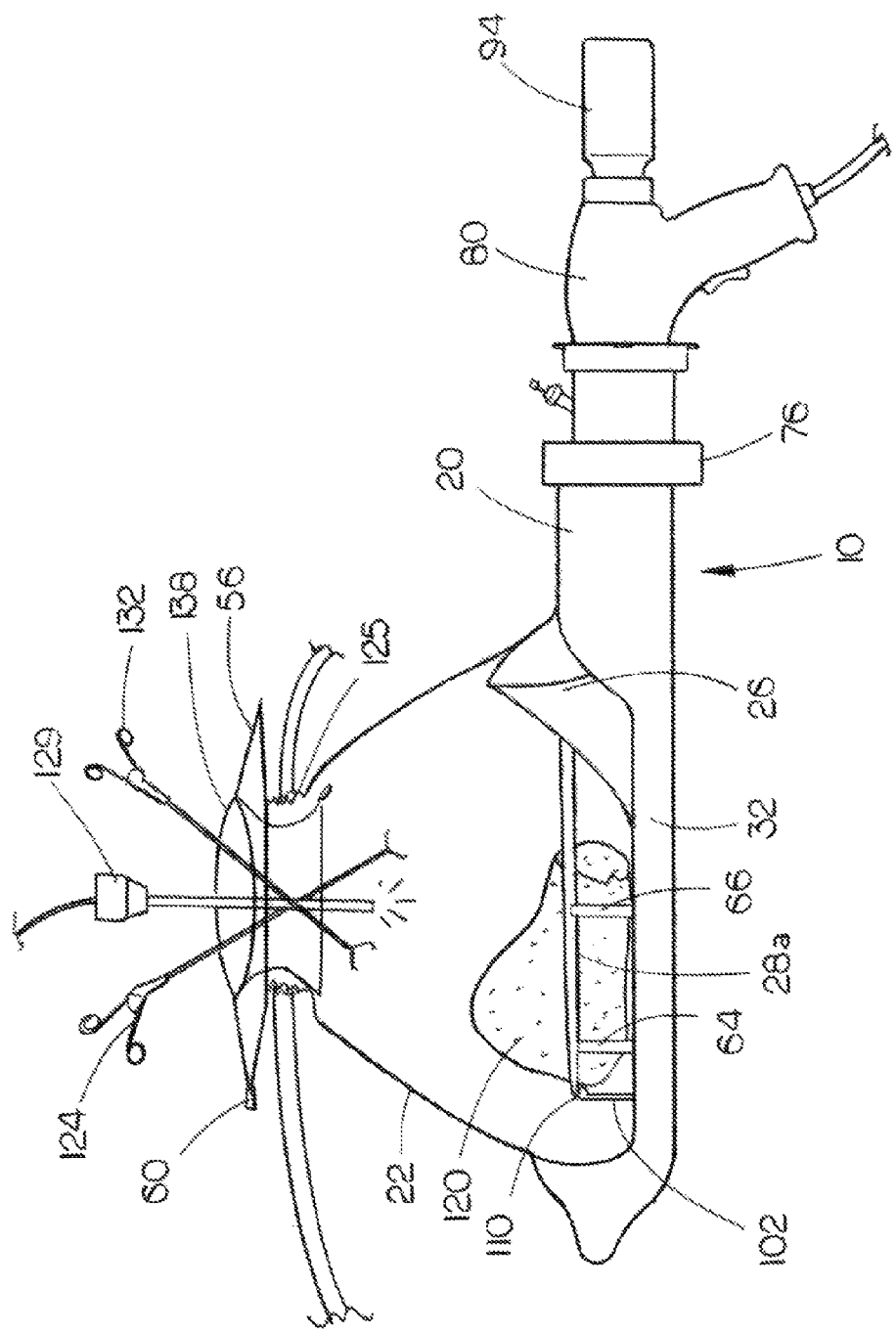
FIG. 11 is a side elevational view of the assembly of FIG. 1 showing a single port device inserted through an opening in the patient's abdomen and through an opening in the bag.

When grasper 102 is inserted into cavity 44, it may be moved into the second position 106, as shown in FIGS. 10 and 11, so that it can assist in pulling tissue 120 into morcellator blade 86 (FIG. 5) to be cut. After the tissue 120 is cut by blade 86, grasper 102 further assists in pulling the tissue through the hollow interior 86a of morcellator blade 86 and out through the valve 92 at the end of morcellator 80, as shown in FIG. 12A. When the grasper 102 is in the second position 106, it is shaped like an inverted "L" with a section 108 extending upward perpendicular from shaft 100 and a section 110 extending outward from section 108 spaced above shaft 100 in a direction that is parallel to shaft 100. Section 110 may act as a barb to engage tissue to assist in guiding the tissue into contact with morcellator blade 86 and through the hollow interior 86a of blade 86.

In addition, shield 20 (FIG. 1) may include an enclosed or semi-enclosed channel (not shown) adjacent to bottom 18 that receives the grasper 102 and shaft 100 as it is inserted through morcellator 80 into cavity 44. The channel (not shown) may assist in guiding the grasper 102 and shaft 100 into a desired location within cavity 44 and preventing the grasper 102 and shaft 100 from contacting and puncturing bag 22.

Figure 12B:
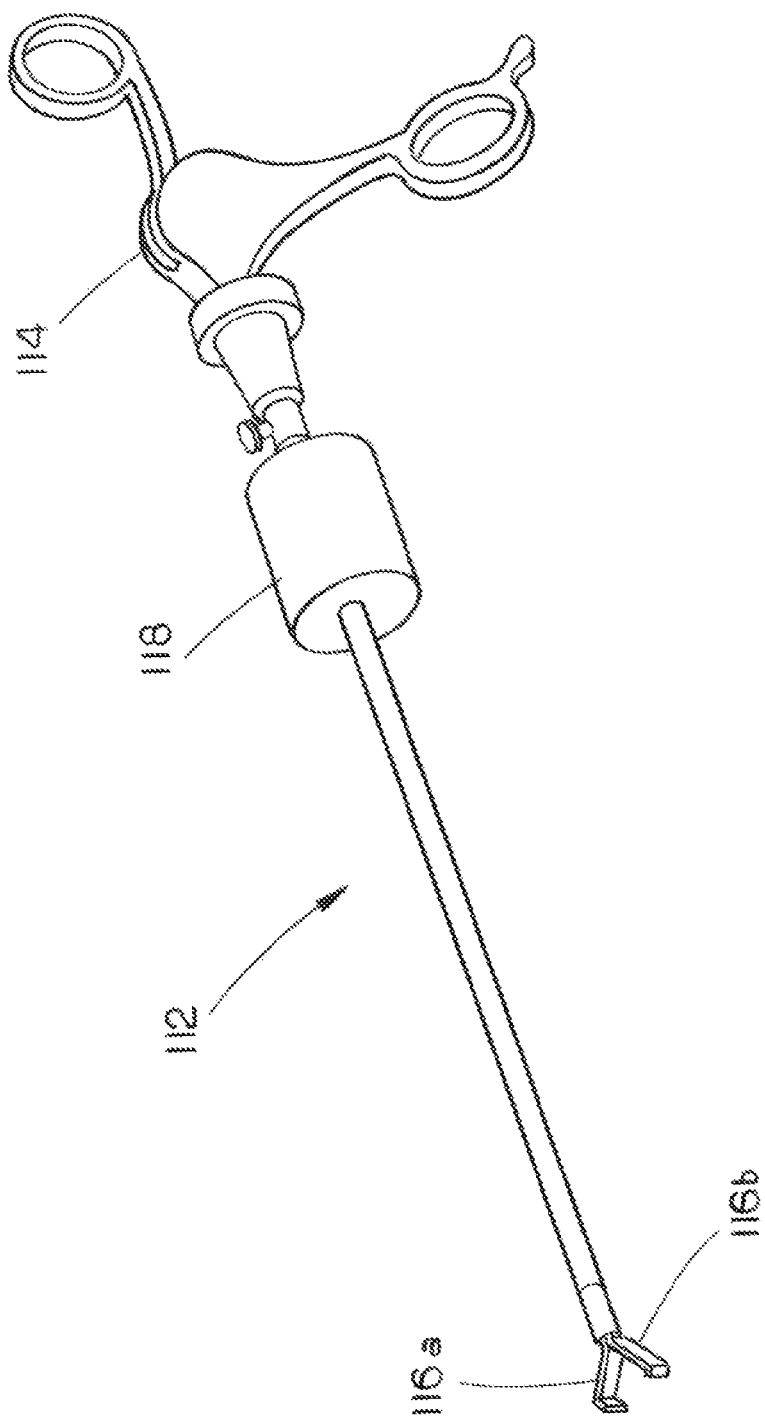
FIG. 12B is a side elevational view of a tenaculum with stabilizer.

Referring to FIG. 12B, a tenaculum 112 may also be inserted through valve 92 and the hollow interior 86a of morcellator blade 86 into cavity 44 to manipulate tissue within the cavity 44 and pull the tissue into contact with morcellator blade 86 and through the hollow interior 86a of blade 86. Tenaculum 112 includes a handle 114 that is connected to and operable to move a pair of graspers 116a-b in a known manner. Tenaculum 112 also includes a stabilizer 118 similar to the stabilizer 98 of instrument 94. Stabilizer 118 is insertable into a channel within morcellator 80, and stabilizer 118 has an outer diameter that is substantially equal to the diameter of the morcellator channel so that stabilizer 118 prevents movement of tenaculum 112 in a direction that is perpendicular to the longitudinal axis 29 of assembly 10. In this manner, stabilizer 118 prevents graspers 116a and 116b from moving into contact with and puncturing bag 22. Stabilizer 118 also engages a stop (not shown) within morcellator 80 to prevent graspers 116a and 116b from extending beyond lower guide 32 into a position where they may puncture bag 22.

In operation, assembly 10 is used to assist in removal of tissue from within a body cavity. While assembly 10 may be used for the removal of any particular tissue in any body cavity, in one embodiment assembly 10 is preferably used to remove a uterus 120 (FIG. 10) from within a patient's peritoneal cavity. Thus, the below description of the preferred operation of assembly 10 describes a hysterectomy procedure using assembly 10, morcellator 80, and instrument 94.

The uterus 120 is first severed from the patient using conventional techniques so that it is freely moveable within the peritoneal cavity 122 (FIG. 10). The uterus 120 may be severed along with the patient's entire cervix, in which case assembly 10 would preferably have an outer diameter of between approximately 30-35 mm for insertion into the peritoneal cavity 122 through the location where the cervix used to be positioned. Alternatively, the uterus 120 may first be severed from the cervix before the transition zone of the cervix is cored through. In this case, assembly 10 would preferably have an outer diameter of approximately 15 mm for insertion through the cored out cervix.

After the uterus 120 is severed in either manner discussed above, assembly 10 is inserted into the patient's vaginal opening with the distal end 14 being advanced first into the patient's peritoneal cavity 122 (either through the opening where the cervix used to be or through the cored out cervix) and the proximal end 12 being positioned outside of the patient. Bag 22 is then deployed from the cavity 44 of shield 20. In order to deploy bag 22, as discussed above, clamp 74 is released and cord 68 is pulled through the clamp 74. The cord 68 breaks the loose connection between arms 64 and 66 and bag 22, which allows the bag 22 to expand from cavity 44. Wings 28a-b may assist in expanding bag 22 from cavity 44. An instrument inserted through an opening in the patient's abdomen may also grab one of tabs 60 and 62 and pull it to deploy bag 22 from cavity 44.

Referring to FIG. 2, once bag 22 is expanded, the uterus 120 is moved through the opening 56 of bag 22 and into cavity 44 using conventional laparoscopic instruments inserted through openings in the patient's abdomen. Assembly 10 is oriented within the patient so that lower guide 32 is positioned below bag 22. In this orientation, when uterus 120 is inserted into bag 22, gravity may allow the uterus 120 to rest on the lower guide 32. As uterus 120 is placed in cavity 44, wings 28a-b may flex to provide room within cavity 44 for uterus 120.

Figure 8A:
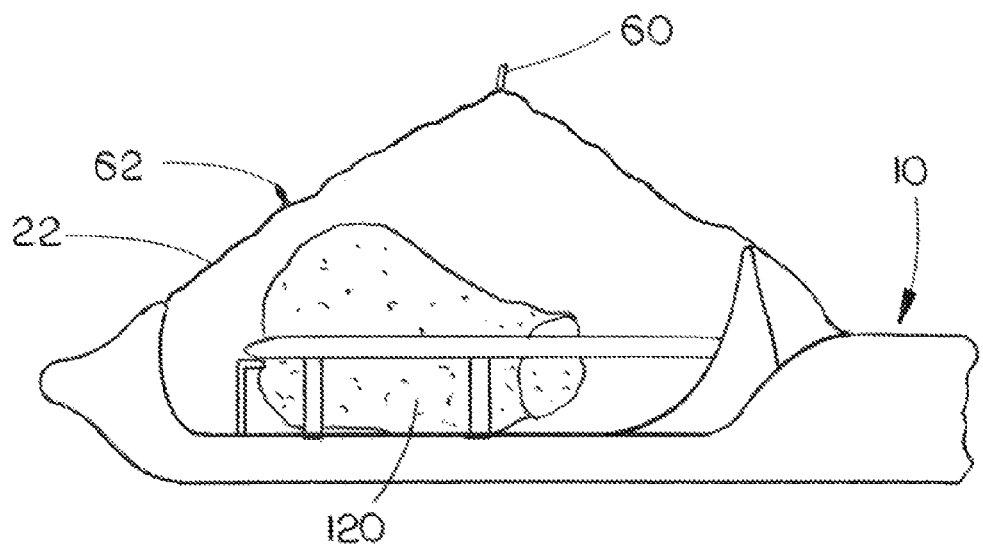
FIGS. 8A-8D show steps for deploying the bag of the assembly of FIG. 1.
Figure 8B:
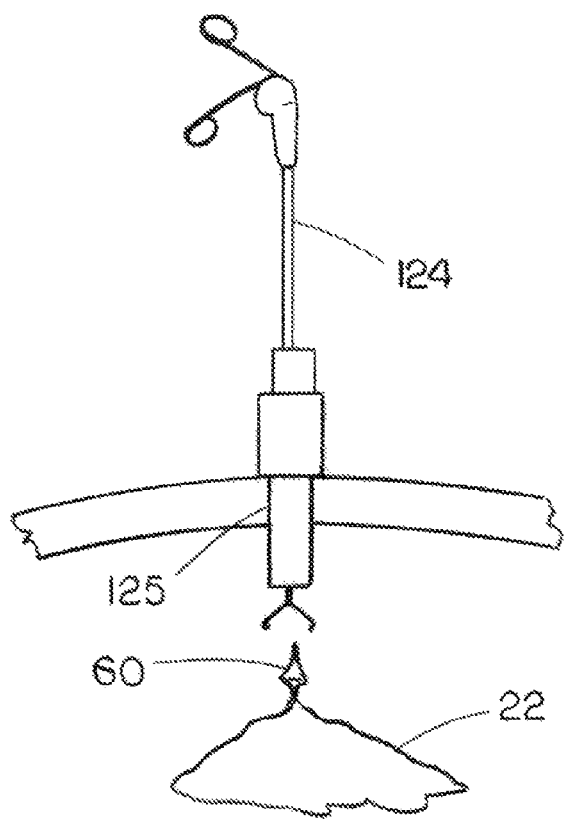
Figure 8C:
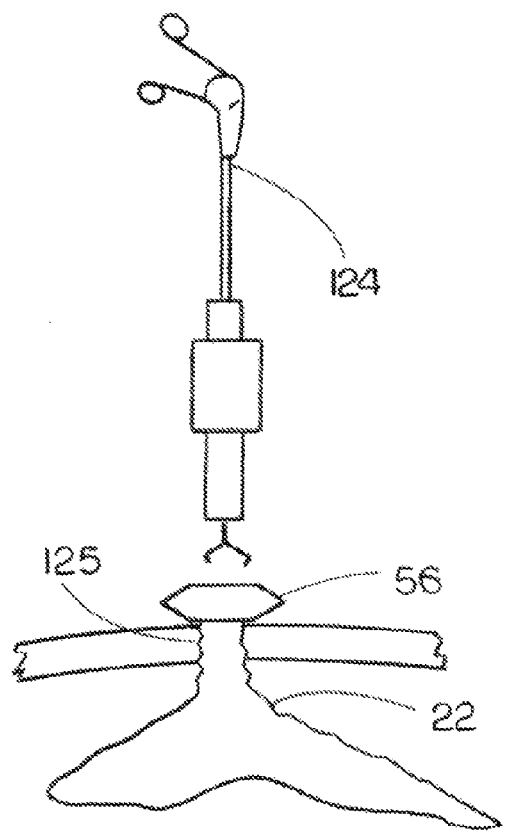
Figure 8D:
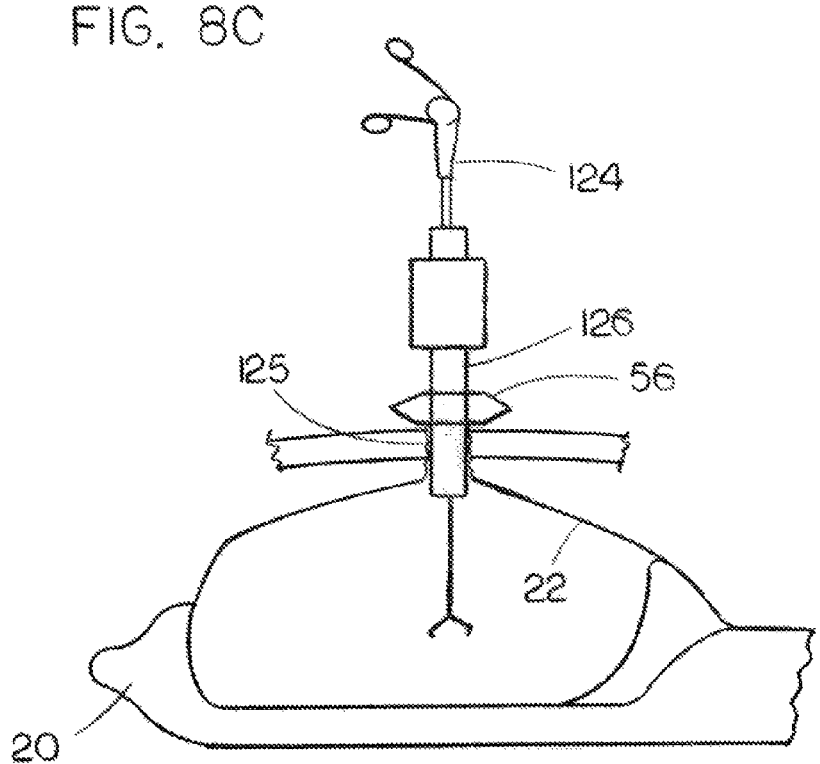

FIG. 8A shows uterus 120 positioned within the interior of bag 22. Once uterus 120 is within bag 22, a laparoscopic instrument 124 inserted through an opening in the patient's abdomen grasps tab 60, as shown in FIG. 8B. Tab 60 is pulled by the instrument 124 through the opening 125 in the patient's abdomen until the entire first opening 56 of bag 22 is pulled through the opening 125 in the patient's abdomen and positioned outside of the patient, as shown in FIG. 8C. The bag 22 is pulled through the opening 125 until the portion of the bag 22 within the patient's abdominal cavity is relatively taut and tented between shield 20 and the opening 125, as shown in FIG. 8D. A trocar sleeve 126 is then inserted through the opening 56 in the bag 22 and the opening 125 in the patient. When the trocar sleeve 126 is inserted, it fixes the bag 22 relative to the opening 125 in the patient so that the bag 22 will not retract through the opening 125. A camera 129 (FIG. 7) is also preferably inserted laparoscopically into the patient's abdomen so that the surgeon can see tab 60 and grasp it with instrument 124.

After trocar sleeve 126 is inserted through openings 56 and 125, the process is repeated to pull second opening 58 of bag 22 through a separate opening 128 (FIG. 9) in the patient's abdominal wall. The laparoscopic instrument 124 is inserted through opening 128 and grasps tab 62, which is pulled through opening 128 until the entire second opening 58 is positioned outside of the patient. Tab 62 is pulled until bag 22 is relatively taut and tented between shield 20 and the opening 128 in the patient. Another trocar sleeve 130 is inserted through the second opening 58 in bag 22 and opening 128 in the patient. Trocar sleeve 130 fixes the bag 22 relative to the patient so that the bag 22 does not retract through the opening 128.

With trocar sleeves 126 and 130 positioned through openings 56 and 58, respectively, referring to FIG. 10, laparoscopic instrument 124 is preferably inserted through trocar sleeve 130 and camera 129 is inserted through trocar sleeve 126. FIG. 10 shows an additional laparoscopic instrument 132 inserted through another trocar sleeve 134 that passes through a third opening 136 in the patient's abdominal wall. Bag 22 may have a third opening (not shown) with a tab (not shown) that is pulled through opening 136 in a similar manner as described above with respect to the other two openings. Trocar sleeve 134 would then be inserted through the third opening (not shown) in bag 22 and opening 136. Alternatively, trocar sleeve 134 may be positioned within the peritoneal cavity 122 outside of bag 22 so that instrument 132 may be used to manipulate the outside of bag 22, if necessary.

After bag 22 is tented and pulled relatively taut between shield 20 and the openings 125 and 128 in the patient's abdominal wall, as shown in FIG. 10, morcellator 80 is connected to assembly 10. Tenting the bag 22 and pulling it relatively taut in this manner spaces it away from tissue 120 and the blade 86 of morcellator 80, which is positioned below hood 26, so that the bag 22 does not come into contact with blade 86 as it slices tissue 120. It is also not necessary to pressurize the interior of bag 22 during the procedure. Morcellator blade 86 is inserted through the opening 36 and valve 40 (FIG. 4) of assembly 10 so that the cutting edge 88 is approximately in the position shown in FIG. 5. Morcellator connector 78 (FIG. 12A) engages the connector 84 on morcellator 80 to releasably couple morcellator 80 and assembly 10.

Referring to FIGS. 10 and 12A, instrument 94 is inserted through the valve 92 of morcellator 80 and through the hollow interior 86a (FIG. 5) of morcellator blade 86 so that the L-shaped grasper 102 is positioned near distal end 14 of assembly 10. L-shaped grasper 102 is moved into the second position 106, shown in FIG. 12A, so that it may engage the uterus 120. Section 110 of grasper 102 may pierce the tissue of the uterus 120. The morcellator blade 86 is activated so that it rotates and is capable of cutting the uterus 120 into tissue strips. As the blade 86 rotates, the instrument 94 is pulled in a direction that retracts it from morcellator 80 (left to right in FIG. 12A) so that the L-shaped grasper 102 pulls the uterus 120 into contact with morcellator blade 86. The morcellator blade 86 cuts the uterus 120 into tissue strips that may be removed from the patient through the hollow interior 86a of blade 86 and the valve 92 (FIG. 12A) of morcellator 80. The wings 28a-b and lower guide 32 in combination form a track that assists in retaining the uterus 120 and guiding the uterus 120 into morcellator blade 86 as the blade 86 cuts the uterus 120 and instrument 94 pulls the uterus 120 to the blade 86. Laparoscopic instruments 124 and/or 132 may also be used to grasp the uterus 120 and push or pull it toward blade 86. The hood 26, wings 28a-b, and lower guide 32, in combination with the tenting of bag 22 between shield 20 and the openings 125 and 128 in the patient's abdominal wall, also form a protective shield that prevents bag 22 from making contact with morcellator blade 86 as it rotates to cut uterus 120. The morcellator blade 86 is preferably sized such that it can cut an average size uterus 120 into pieces that can be removed from the patient's vaginal opening in approximately 10 minutes.

As the morcellator blade 86 cuts uterus 120, any particles and/or fluid from the uterus 120 are contained within the assembly 10 due to bag 22. This ensures that all portions of the uterus 120 are removed from the patient's body upon completion of the procedure even those that may spin away from blade 86.

As shown in FIG. 12A, after the uterus 120 has been cut by morcellator blade 86 and pulled through the hollow interior 86a of the blade 86, the cut particles of uterus 120 are pulled through morcellator 80 and out of valve 92 with instrument 94.

After the uterus 120 is pulled out of the morcellator 80, trocar sleeves 126, 130, and 134 are retracted through the respective openings 125, 128, and 136 along with camera 129 and instruments 124 and 132. The openings 56 and 58 of bag 22 are then closed. The openings 56 and 58 may be closed with a slide lock device, as described above. The openings 56 and 58 may also be closed simply by tying a knot in the bag 22 near the openings 56 and 58 or slipping a rubber band over the openings 56 and 58. The openings 56 and 58 are closed so that no material within bag 22 leaks into the patient's peritoneal cavity 122 as assembly 10 is retracted from the patient. The openings 56 and 58 of the bag 22 are pushed back through the openings 125 and 128 in the patient so that the entire bag 22 is positioned within the peritoneal cavity 122. The bag 22 is then pushed back into the cavity 44 within the shield 20. Laparoscopic instrument 124 may be reinserted into the peritoneal cavity 122 to assist in pushing bag 22 into cavity 44.

Assembly 10 is then removed from the patient through the vaginal opening or cervical opening. Any particles and fluid from the uterus 120 that are contained within the bag 22 are removed from the patient along with assembly 10.

In addition to being inserted into a body cavity through a vaginal opening, assembly 10 may be inserted into a body cavity laparoscopically or by any other known procedure.

Referring to FIG. 11, an alternative use of assembly 10 is illustrated. In FIG. 11, bag 22 is shown with only one opening 56 for use with a single port device 138 that is inserted through opening 56 and opening 125 in the patient's abdominal cavity. As is known in the art, single port device 138 is larger than the trocar sleeves 126, 130, and 134, shown in FIG. 10, and is able to accommodate insertion of camera 129 and laparoscopic instruments 124 and 132 through the opening 125 in the patient and into bag 22. Thus, bag 22 only needs a single opening 56 for the single port device 138. Removal of tissue 120 with the assembly 10 configured for use with the single port device 138 is otherwise carried out as described above.

An instrument in accordance with the present invention comprises a stabilizer, a shaft extending from the stabilizer, and a tool coupled to the shaft.

The instrument described above, wherein the tool comprises a grasper moveable between a first position in which it is substantially parallel to the shaft and a second position in which it extends upward from the shaft and is substantially perpendicular to the shaft.

The instrument described above, wherein the stabilizer is configured to be received by a channel within a morcellator.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A morcellator shield and bag assembly comprising:
 a shield comprising:
  a first section comprising a peripheral edge at a first end and a first opening at a second end, wherein the first section surrounds a hollow interior space that forms at least a portion of a cavity of the shield, and wherein the first opening and the hollow interior space are configured to receive a morcellator blade of a morcellator, and
  an elongate guide that is joined to the peripheral edge at the first end of the first section and that extends away from the first section, wherein the elongate guide extends outward from only a portion of the peripheral edge such that the elongate guide does not surround an interior space, wherein the elongate guide forms a second opening in the shield, and wherein the cavity is in fluid communication with the first and second openings;

a morcellator connector joined to the second end of the shield, wherein the morcellator connector is configured for releasable connection with a morcellator; and a bag coupled to the elongate guide adjacent the second opening and moveable between a contracted position, in which at least a portion of the bag is positioned within the cavity and an expanded position, wherein the bag comprises a first end that is attached to a surface of the elongate guide when the bag is in the contracted position and when the bag is in the expanded position, and wherein the first end of the bag surrounds the second opening in the shield when the bag is in the contracted position and when the bag is in the expanded position, wherein the bag comprises a second end with an opening that is in fluid communication with the cavity when the bag is in the expanded position, wherein the second end of the bag is spaced from the first end of the bag when the bag is in the expanded position, and wherein the elongate guide is configured for insertion into a body cavity and to support body tissue placed through the opening of the bag when the bag is in the expanded position.

2. The assembly of claim 1, wherein the opening of the bag is moveable between an open position and a closed position.

3. The assembly of claim 1, wherein the second end of the bag is positioned outside of the cavity when the bag is in the expanded position.

4. The assembly of claim 1, wherein the shield comprises a rigid portion and a flexible hood joined to the rigid portion.

5. The assembly of claim 4, wherein the rigid portion comprises the first section and the elongate guide.

6. The assembly of claim 5, wherein the first section is cylindrical.

7. The assembly of claim 5, wherein the flexible hood is joined to the first end of the first section.

8. The assembly of claim 5, wherein the bag is joined to the flexible hood.

9. The assembly of claim 5, wherein the bag is joined to an outer surface of the elongate guide and to an outer surface of the flexible hood.

10. The assembly of claim 5, wherein the first section and elongate guide comprise an inner surface, and wherein the inner surface comprises a step positioned between the elongate guide and the first section.

11. The assembly of claim 1, wherein the bag comprises at least one tab that is positioned adjacent the opening in the bag.

12. The assembly of claim 1, wherein the shield comprises a rigid portion and flexible wings joined to the rigid portion, wherein the flexible wings are moveable between a contracted position and an expanded position, wherein the flexible wings are in the contracted position when the bag is in the contracted position, and wherein the flexible wings are in the expanded position when the bag is in the expanded position.

13. The assembly of claim 12, wherein the bag is joined to an outer surface of each of the flexible wings and to an outer surface of the rigid portion.

14. The assembly of claim 1, wherein the bag comprises a second opening that is in fluid communication with the cavity when the bag is in the expanded position.

15. The assembly of claim 1, wherein the combination of the bag and the shield comprises a proximal end and a distal end, wherein the first opening is positioned adjacent the proximal end.

16. A method of removing tissue from a body cavity using a morcellator and a morcellator shield and bag assembly comprising a proximal end and a distal end, a shield comprising a first section that forms at least a portion of a cavity of the shield, wherein the first section presents a first opening positioned adjacent to the proximal end, wherein the shield comprises an elongate guide that is joined to and extends away from the first section, wherein the elongate guide forms a second opening in the shield, and a bag coupled to the shield and moveable between a contracted position, in which at least a portion of the bag is positioned within the cavity and an expanded position, wherein the bag comprises a first end that is attached to a surface of the elongate guide when the bag is in the contracted position and when the bag is in the expanded position, and wherein the first end of the bag surrounds the second opening in the shield when the bag is in the contracted position and when the bag is in the expanded position, wherein the bag comprises a second end with an opening that is in fluid communication with the cavity when the bag is in the expanded position, wherein the second end of the bag is spaced from the first end of the bag when the bag is in the expanded position, comprising:

inserting at least a portion of the morcellator shield and bag assembly into a body cavity through a vaginal opening of a patient;

moving the bag to the expanded position;

placing tissue in the bag through the opening in the bag;

pulling at least a portion of the bag through another opening in the patient;

inserting at least a portion of the morcellator into the morcellator shield and bag assembly through the first opening of the shield and into the cavity of the shield; and morcellating the tissue with the morcellator.

17. The method of claim 16, further comprising:
removing the morcellator from the morcellator shield and bag assembly;
closing the opening in the bag;
moving the bag to the contracted position; and
removing the morcellator shield and bag assembly from the body cavity along with all portions of the tissue.

18. The method of claim 16, further comprising:
pulling the opening of the bag through the other opening in the patient; and
inserting an instrument through the opening of the bag and through the other opening in the patient.

19. The method of claim 16, further comprising:
inserting an instrument into the morcellator shield and bag assembly;
guiding the tissue into the morcellator with the instrument; and
removing the tissue from the morcellator shield and bag assembly with the instrument.

20. The method of claim 16, wherein the tissue is a uterus, wherein the body cavity is a peritoneal cavity, and wherein the morcellator shield and bag assembly is inserted into the peritoneal cavity through the vaginal opening.

21. The method of claim 16, wherein the shield prevents the morcellator from contacting the bag, and wherein the tissue is contained with the morcellator shield and bag assembly as the morcellator morcellates the tissue.

22. The assembly of claim 1, wherein the bag is joined to an outer surface of the elongate guide, and wherein the bag is not positioned within the cavity when the bag is in its expanded position.

23. The assembly of claim 1, wherein the bag moves from its contracted position to its expanded position through the second opening.

24. A morcellator shield and bag assembly comprising:
a shield comprising a first section that forms at least a portion of a cavity of the shield, wherein the first section comprises an end with first opening that is in fluid communication with the cavity, wherein the first opening and the cavity are configured to receive a morcellator blade of a morcellator, wherein the shield comprises an elongate guide that is joined to and extends away from the first section, wherein the elongate guide forms a second opening in the shield;
a morcellator connector joined to the end of the shield, wherein the morcellator connector is configured for releasable connection with a morcellator; and
a bag coupled to an outer surface of the shield and moveable between a contracted position, in which at least a portion of the bag is positioned within the cavity and an expanded position, wherein the bag comprises a first end that is attached to a surface of the elongate guide when the bag is in the contracted position and when the bag is in the expanded position, and wherein the first end of the bag surrounds the second opening in the shield when the bag is in the contracted position and when the bag is in the expanded position, wherein the bag comprises a second end with an opening that is in fluid communication with the cavity when the bag is in the expanded position, wherein the second end of the bag is spaced from the first end of the bag when the bag is in the expanded position, and wherein no portion of the bag is positioned within the cavity when the bag is in the expanded position.

25. The assembly of claim 24, wherein the shield comprises a rigid portion and a flexible hood joined to the rigid portion.

26. The assembly of claim 25, wherein the bag is joined to an outer surface of the elongate guide and to an outer surface of the flexible hood.

27. The assembly of claim 24, wherein the shield comprises a rigid portion and flexible wings joined to the rigid portion, wherein the flexible wings are moveable between a contracted position and an expanded position, wherein the flexible wings are in the contracted position when the bag is in the contracted position, and wherein the flexible wings are in the expanded position when the bag is in the expanded position.

* * * * *